United States Patent [19]

Rogalsky

[11] Patent Number: 5,270,205
[45] Date of Patent: Dec. 14, 1993

[54] DEVICE FOR GROWING CELLS

[76] Inventor: Alena Rogalsky, 186 Pinehurst Ave., New York, N.Y. 10033

[21] Appl. No.: 40,834

[22] Filed: Mar. 31, 1993

Related U.S. Application Data

[63] Continuation-in-part of Ser. No. 874,550, Apr. 20, 1992, abandoned, which is a continuation of Ser. No. 495,104, Mar. 19, 1990, abandoned.

[51] Int. Cl.$^5$ ............................................. C12M 3/04
[52] U.S. Cl. ....................................... 435/285; 435/296; 435/310; 435/312; 435/316; 435/813; 422/102; 422/224; 422/275
[58] Field of Search ............... 422/135, 224, 275, 209, 422/102; 435/285, 286, 296, 303, 306, 310, 312, 316, 813

[56] References Cited

U.S. PATENT DOCUMENTS

| | | | |
|---|---|---|---|
| 2,686,754 | 8/1954 | Monod | 435/813 X |
| 3,486,865 | 12/1969 | Furusawa et al. | 422/135 |
| 3,594,277 | 7/1971 | Mako | 435/210 X |
| 3,684,458 | 8/1972 | McCammon et al. | 422/135 |
| 3,839,155 | 10/1974 | McAleer et al. | 435/312 X |
| 3,930,801 | 1/1976 | Pinet | 422/275 X |
| 3,976,431 | 8/1976 | Boggs et al. | 422/135 |
| 4,004,981 | 1/1977 | Hurni et al. | 435/312 X |
| 4,317,886 | 3/1982 | Johnson et al. | 435/285 |
| 4,343,904 | 8/1982 | Birch et al. | 435/310 X |
| 4,377,639 | 3/1983 | Lee | 435/286 X |
| 4,446,236 | 5/1984 | Clyde | 435/813 X |
| 4,912,048 | 3/1990 | Smith et al. | 435/296 |
| 4,962,033 | 10/1990 | Serkes et al. | 435/285 X |
| 4,985,208 | 1/1991 | Sugawara et al. | 422/135 |
| 4,999,302 | 3/1991 | Kahler et al. | 435/312 X |
| 5,020,916 | 6/1991 | Fritsch | 422/135 X |
| 5,045,470 | 9/1991 | Kloss | 422/224 X |

FOREIGN PATENT DOCUMENTS

| | | | |
|---|---|---|---|
| 320348 | 6/1989 | European Pat. Off. | 435/285 |
| 40-3964 | 3/1965 | Japan | 422/135 |
| 51-38757 | 10/1976 | Japan | 422/135 |
| 965504 | 10/1982 | U.S.S.R. | 422/135 |
| 1123718 | 8/1987 | U.S.S.R. | 422/135 |

*Primary Examiner*—James C. Housel
*Assistant Examiner*—Maureen M. Wallenhorst

[57] ABSTRACT

A device for growing cells has a container which forms an inner chamber, and a plurality of discs located in the inner chamber and provided with corrugations sufficient to entrain a growth medium with cells during a rotation of the container with the discs, while allowing the growth medium with the cells to slowly flow downwardly.

12 Claims, 7 Drawing Sheets

F I G. 7
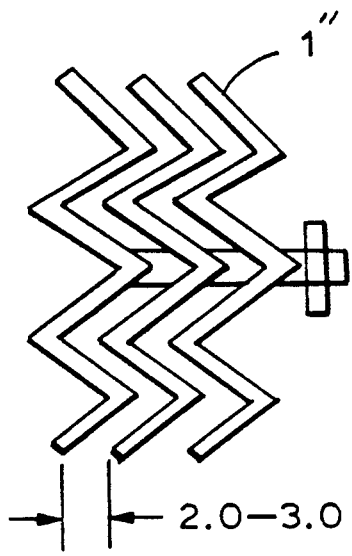
F I G. 8
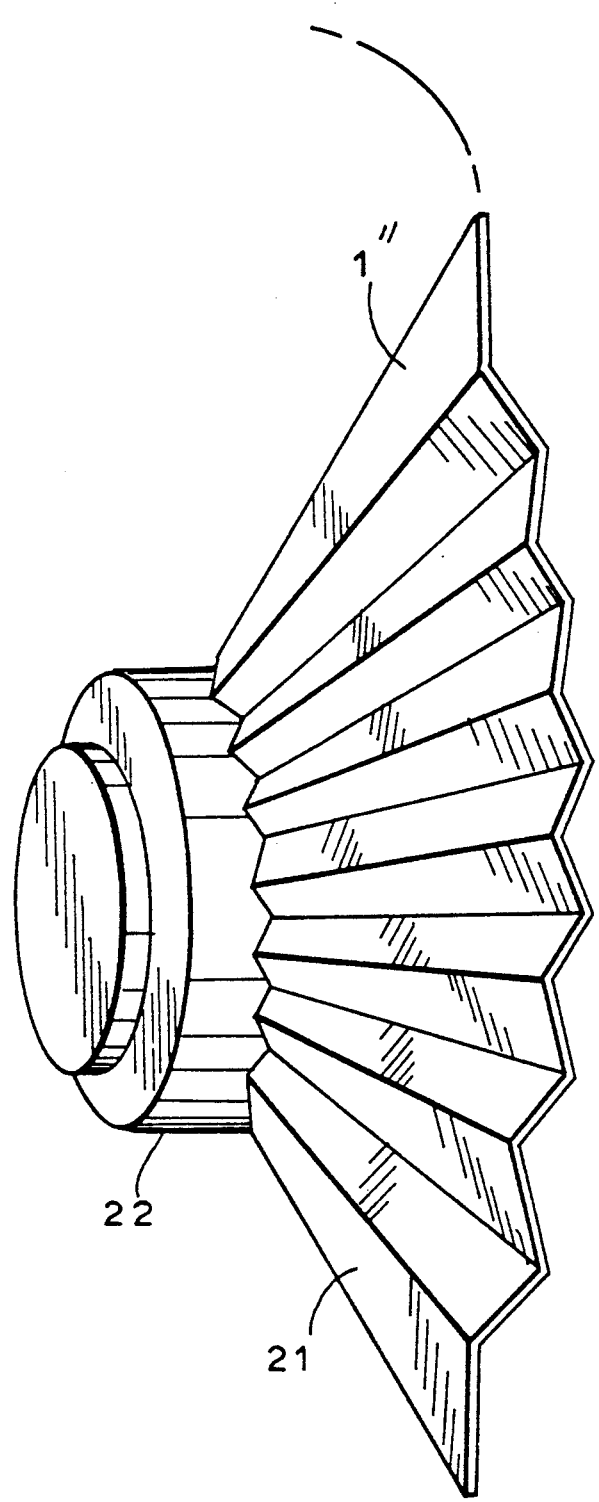

FIG. 9
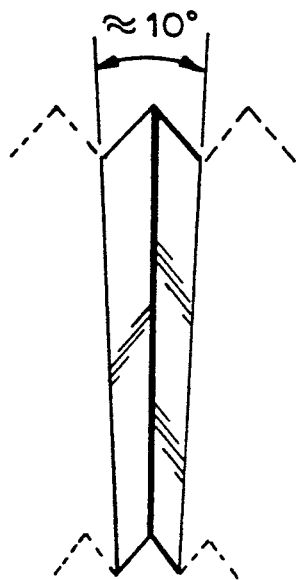
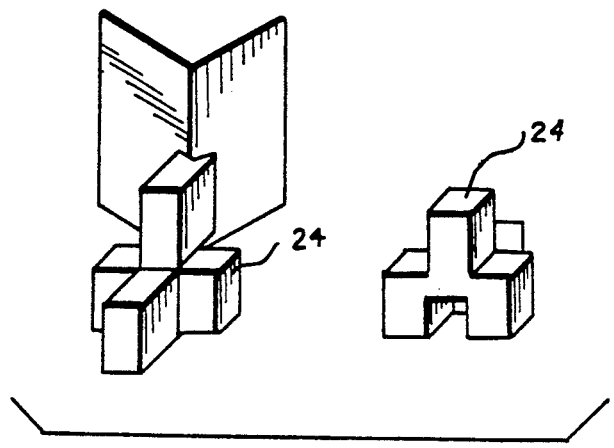
FIG. 10
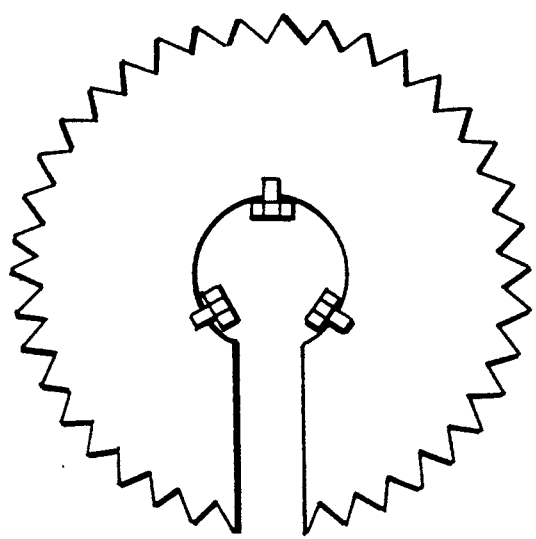
FIG. 11

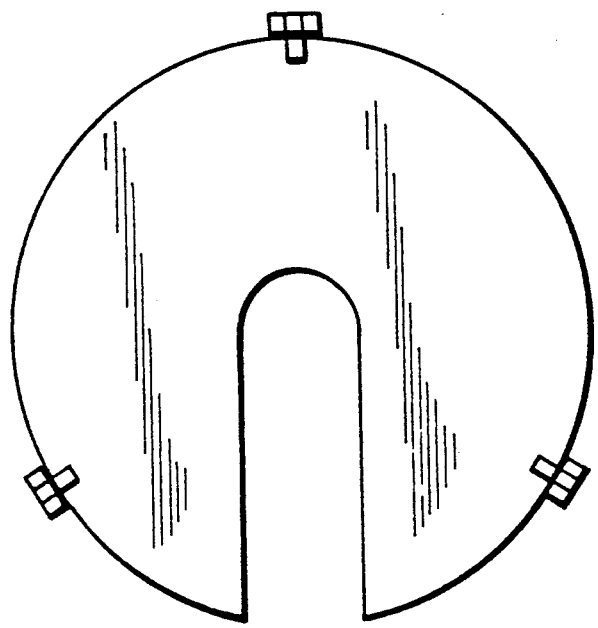
F I G. 12
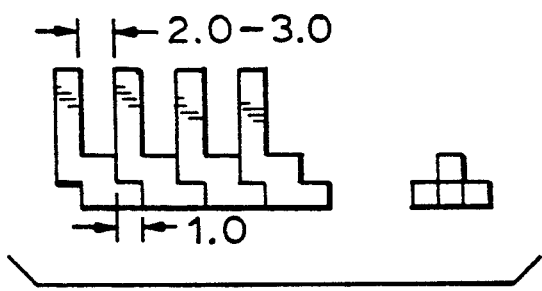
F I G. 13
F I G. 14

DEVICE FOR GROWING CELLS

CROSS REFERENCES TO RELATED APPLICATIONS

This application is a continuation-in-part of patent application Ser. No. 07/874,550, filed on Apr. 20, 1992, now abandoned, which in turn is a continuation of patent application Ser. No. 07/495,104 filed on Mar. 19, 1990, now abandoned.

BACKGROUND OF THE INVENTION

The present invention relates to devices for growing cells, and more particularly to cylindrical devices which are slowly rotated during growing cells.

Devices of the above mentioned general type are known in the art. The known devices include usually cylindrical bottles with or without inner discs, inserts, etc., and in some of them the walls, the cylindrical inserts have uneven surfaces. The devices of this type should have an extended surface for growing cells, a simple construction, optimal conditions for aeration of cells, low consumption of a growth medium and a cell removing substance. etc. The above listed requirements are not always satisfied in the existing devices of this type. It is therefore believed that a further improvement of the existing devices in these aspects is desirable.

SUMMARY OF THE INVENTION

Accordingly, it is an object of the present invention to provide a device for growing cells, which is a further improvement of the existing devices.

More particularly, it is an object of the present invention to provide a device for growing cells which has an extended surface for growing cells, is easy and simple to manufacture, requires a reasonable quantity of a growth medium and a cell removing substance, provides good conditions for cell aeration.

In keeping with these objects and with others which will become apparent hereinafter, one feature of the present invention resides, briefly stated, in a device for growing cells, which has a cylindrical container having an axis and forming an inner chamber, and a plurality of discs for supporting cells, wherein the discs are spaced from one another in an axial direction and arranged in the inner chamber of the container substantially coaxially with the container, and each of the discs is provided with a plurality of corrugations sufficient to entrain a growth medium with cells during rotation of the discs around the axis while allowing the growth medium with the cells to move radially inwardly.

When the device is designed in accordance with the present invention, then during the rotation of the discs together with the whole device the corrugations on the discs entrain the growth medium with the cells and transfer them from the bottom of the device upwardly and then the growth medium with the cells slowly flows radially inwardly. As a result, only a small quantity of the growth medium at the bottom of the device is sufficient, the cells uniformly distribute and become attached to the whole surface of the discs, a small quantity of Trypsin for cell removal is also needed, the cells are properly aerated, and the surface for growing cells is substantially increased.

The further advantageous feature of the present invention is that the corrugated discs are located so close to one another that the projections of one disc are partially inserted into the grooves of a neighboring disc, so that a serpentine path for the growth medium is formed. This reduces the speed of the growth medium flow downwardly and thereby contributes to the attachement of the cells to the surfaces of the discs.

The novel features of the present invention are set forth in particular in the appended claims. The invention itself, however, both as to its construction and its method of manufacture will be best understood from the following description of preferred embodiments, which is accompanied by the following drawings

BRIEF DESCRIPTION OF THE DRAWINGS

FIG. 7 shows a disc of the inventive device in accordance with still another embodiment of the present invention;

FIG. 8 is a view showing a disc of the inventive device in accordance with a still further embodiment of the invention;

FIG. 9 is a schematic view showing a fragment of the inventive disc of the embodiment of FIG. 8;

FIG. 10 is a view showing a connecting element for supporting and connecting the discs of the inventive device;

FIGS. 11 and 12 are views showing the discs with the connecting elements in accordance with two further embodiments of the invention;

FIG. 13 is a schematic view showing the area of assembling of the connecting elements and the discs with one another, in the inventive device for growing cells; and FIG. 14 is a view showing still a further modification of the device for growing cells, in accordance with the present invention.

DESCRIPTION OF PREFERRED EMBODIMENTS

Figure 1:
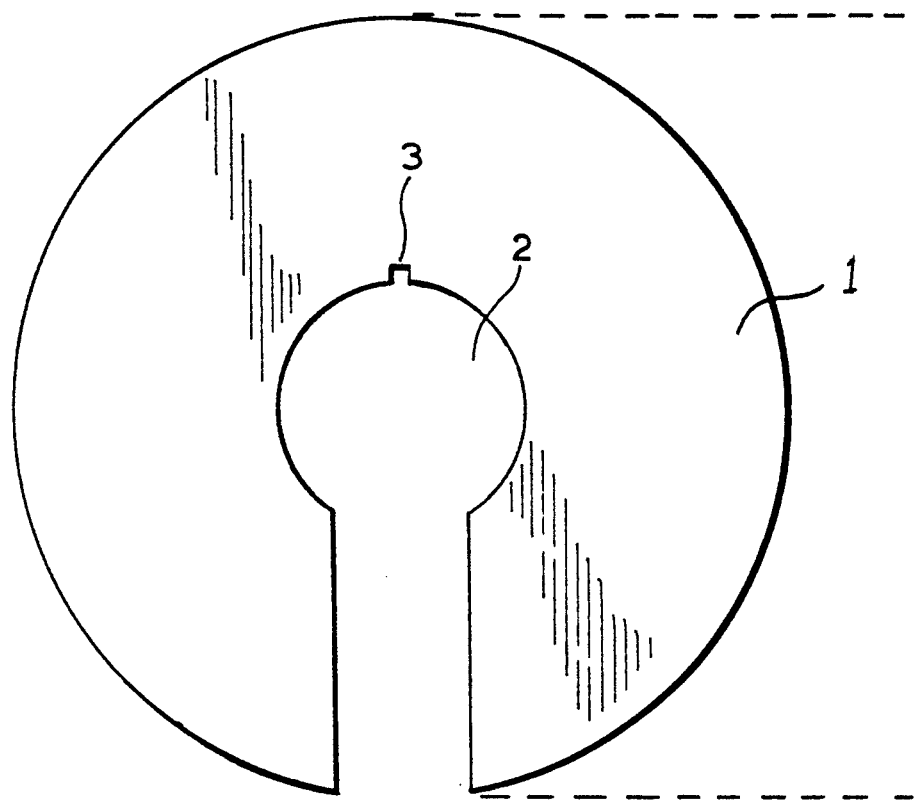
FIG. 1 is a view showing a disc of a device for growing cells in accordance with the present invention.
Figure 2:
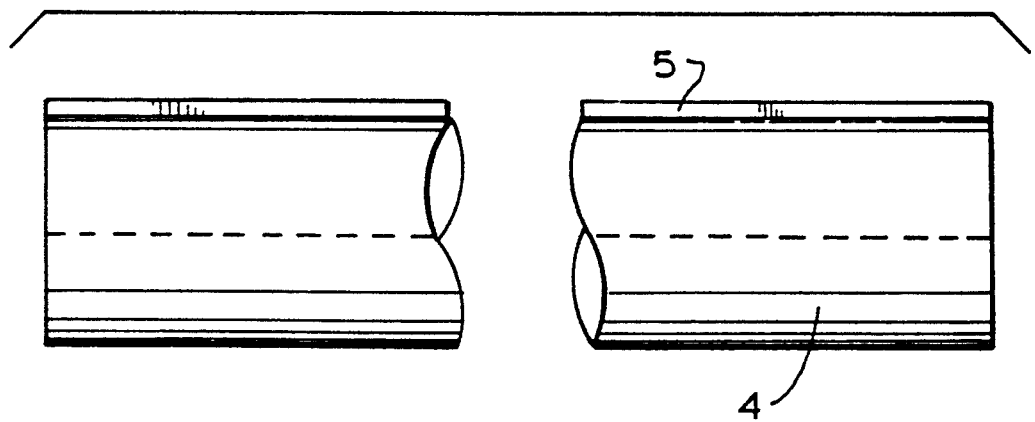
FIG. 2 is a view showing a shaft for supporting a plurality of discs of FIG. 1.
Figure 4:
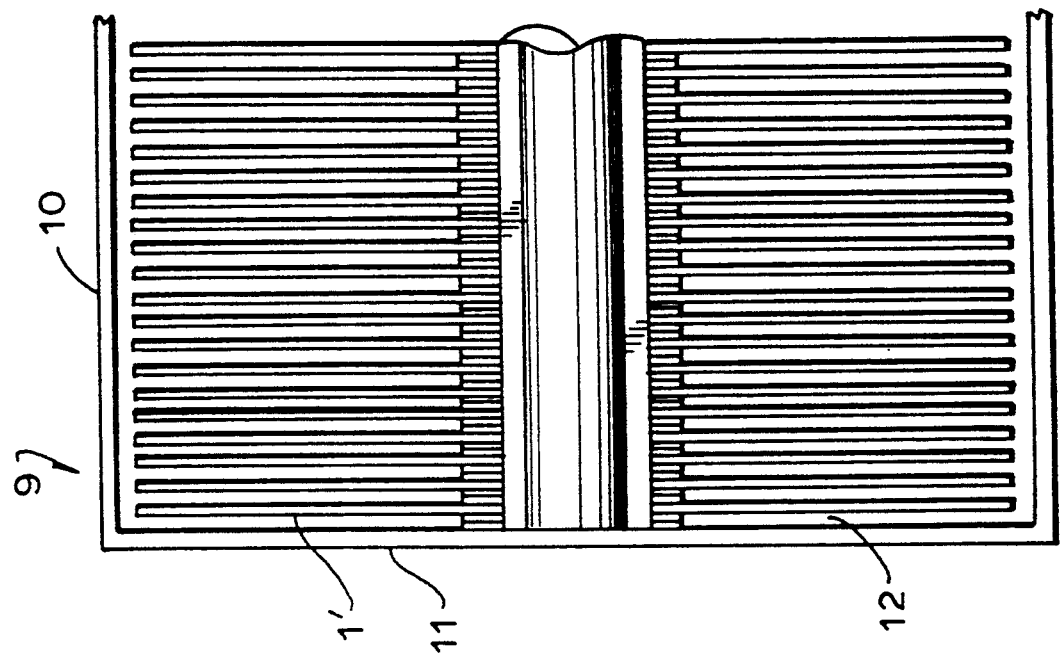
FIG. 4 is a schematic view showing the device for growing cells in the assembled condition.
Figure 3:
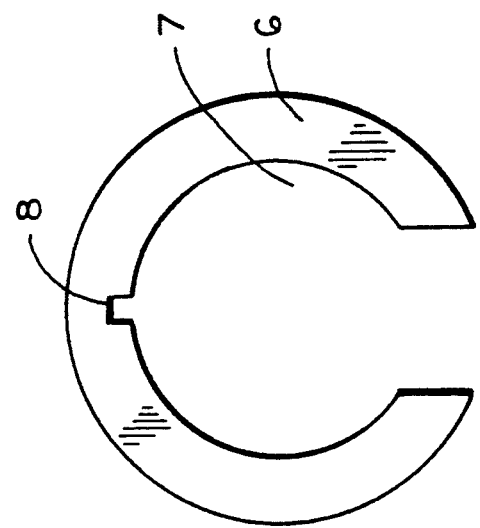
FIG. 3 is a view showing a spacer for providing distances between the discs of the inventive device for growing cells.

A device for growing cells in accordance with the present invention includes a plurality of discs which are identified as a whole with reference numeral 1. Each disc has a central opening 2 and a groove 3 which extends from and opens in the opening 2. The device further includes a shaft 4 for supporting a plurality of the discs 1. The shaft 4 is provided with a projection 5 which substantially corresponds to the groove 3. Further, a plurality of spacers 6 are provided. Each spacer has a central opening 7 and a groove 8 which extends from and opens into the central opening. Finally, the device has a cylindrical container 9 with a cylindrical peripheral wall 10 and two end walls 11. Only one of the walls 11 is shown in FIG. 4. Another wall is not shown and can be provided with a not shown neck for filling a nutrient (growth) solution into an inner chamber 12 formed inside the container 9.

In an assembled condition, the discs 1 are arranged on the shaft 4 so that the projection or key 5 of the shaft 4 extends through the grooves 3 of the discs, and the spacers 6 are placed between the discs 1 so that the projection 5 extends through the grooves 8 of the spacers. The spacers are arranged in the device between the discs and also between the end discs and the end walls 11 of the container. The end discs which are located the closest to the end walls of the container and identified with reference numeral 1' in FIG. 4, can be of a greater diameter than the remaining discs, and more particularly of a diameter corresponding to the inner diameter of the container. It is not necessary to connect the unit including the discs, the shafts and the spacers to the container. The shaft can be of such length that its opposite ends tightly abut against the end walls 11 of the container 9 and therefore the above mentioned unit is held in the container. On the other hand, the spacers which are located between the outermost discs and the end walls 11 of the container can also tightly fit in these spaces and hold the whole unit inside the container without special connectors, welding, glueing, etc.

As can be seen from FIG. 4, the outer diameter of the discs is somewhat smaller than the inner diameter of the peripheral wall 10 of the container 9 so that a sufficient space remains for communication of small subchambers formed between the discs.

Figure 5:
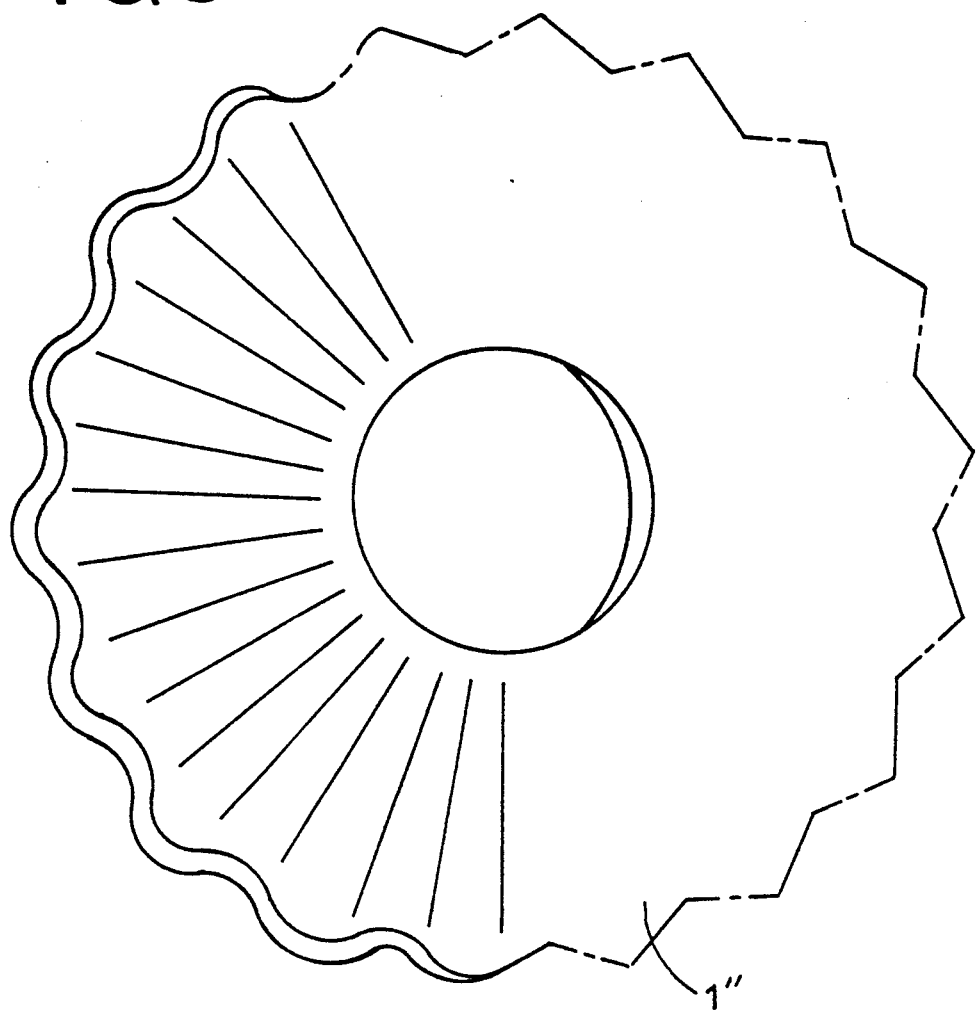
FIG. 5 is a view showing a disc of the inventive device in accordance with a further embodiment of the invention.

As can be seen from a perspective view of FIG. 5, the discs in accordance with the present invention are corrugated or in other words have a wave-shaped surface. Such discs are identified with reference numeral 1''. When the discs in the device for growing cells are corrugated, they provide for highly advantageous results. First of all, the surface of the corrugated discs is substantially greater than the surface of flat discs, and their total surface is much greater than the surface of a corrugated container or corrugated cylindrical inserts of the prior art. When the discs 1'' are provided with corrugations, during rotation of the discs together with the device the corrugations of the discs entrain the growth medium with the cells accommodated in the lower part of the container near its bottom and transport the same upwardly, and then the growth medium with the cells flows slowly radially downwardly over the surfaces of the discs. As a result, only a small quantity of the growth medium, just near the bottom of the container is sufficient to spread over the whole disc surface. The cells are reliably attached to the surfaces of the discs and grow on them. Afterward, again only a small quantity of a cell removing substance (Trypsin) is needed to remove the cells from the discs, since this substance is similarly entrained by the corrugations, transported upwardly during the rotation of the discs, and slowly flows radially inwardly.

Figure 6:
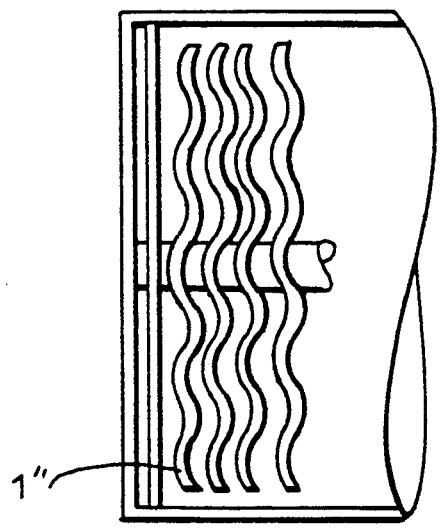
FIG. 6 is a view schematically showing the device of FIG. 5 in the assembled condition.
Figure 6A:
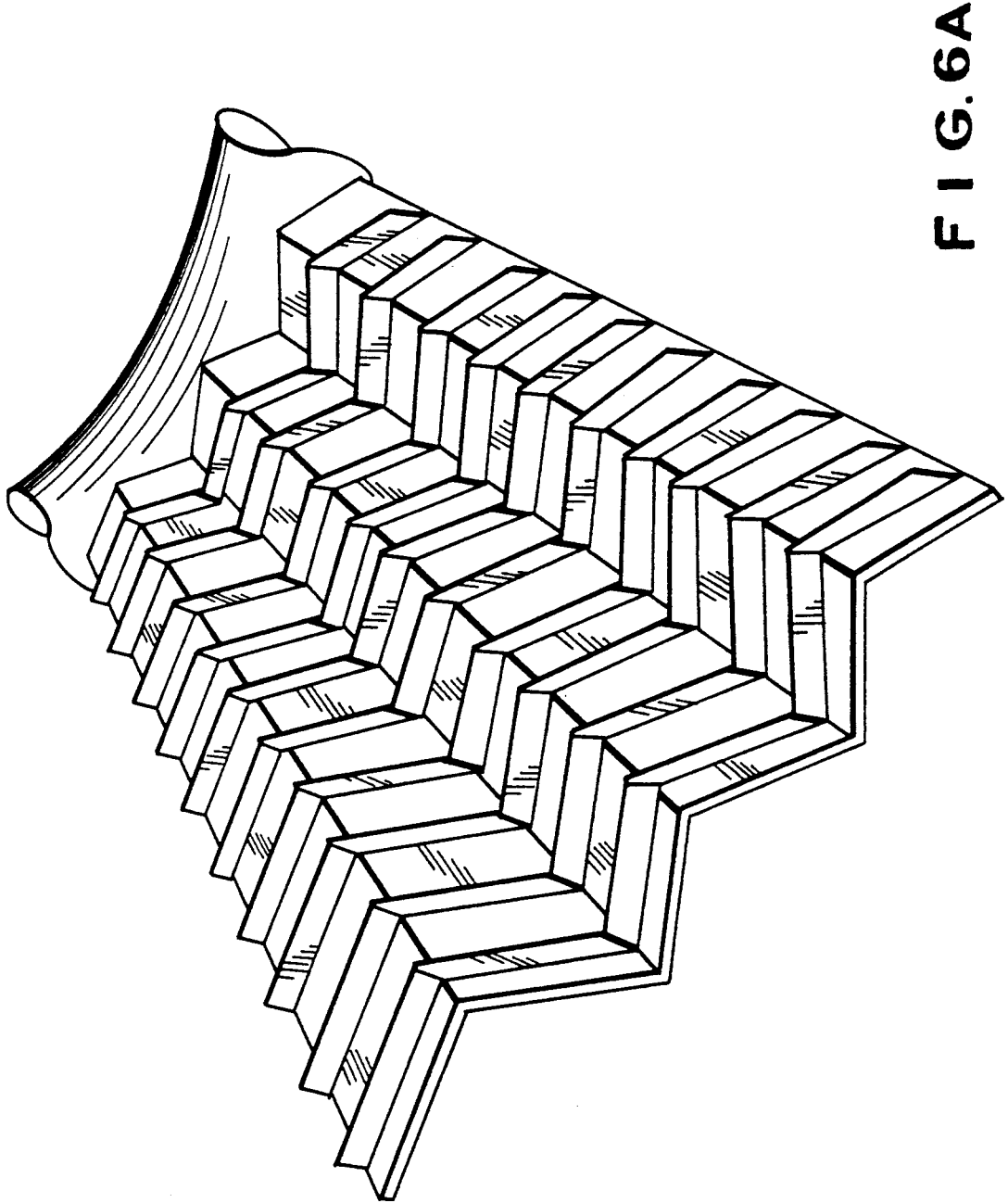
FIG. 6a is a view showing a disc of the inventive device in accordance with another embodiment of the present invention.

As shown in FIGS. 5 and 8, the corrugations of the discs 1'' can extend in a radial direction and be spaced from one another in a circumferential direction. As can be seen from FIG. 6, the corrugations of the discs 1'' can extend in a circumferential direction and be spaced from one another in a radial direction. Finally, as can be seen from FIG. 6a, the corrugations can extend both in the radial direction and in the circumferential direction. The discs can be connected with one another by arranging them on a common shaft.

In the embodiment of FIG. 7, the discs 1'' are also corrugated. The depth of the corrugations is greater than in the above described embodiments. At the same time the discs are nested in one another so that the projections of a preceding disc are inserted in the grooves of a subsequent disc. In this construction a serpentine path for the growth medium is formed between the discs, which further slows down the speed of flowing of the growth medium radially inwardly and thereby contributes to the attachement of the cells to the surfaces of the discs. The discs are assembled on the common shaft.

In the embodiment shown in FIG. 8, the discs 1'' can be assembled in a different manner. Each disc has a disc-shaped portion 21 and a hub-shaped portion 22. The hub-portion 22 is hollow and stepped, and therefore the discs can be assembled with one another by nesting of the hub-shaped portion of the preceding disc in the hub-shaped portion of the subsequent disc. This makes unnecessary the shaft for connecting the discs which is utilized in the preceding embodiments of the inventive device.

It is to be understood that the corrugations on the discs can be formed in a different manner, can be spaced from one another by different distances, and can have different depth, length and angles between their neighboring walls. FIG. 9 shows an angle equal to approximately 10°. However, this angle can vary within a wide range.

FIG. 10 shows an element for connecting the discs with one another. The connecting element is identified with reference numeral 24. It is stepped and has a slot for engaging an edge of a disc. Also, the connecting elements are nestable in one another as shown in FIG. 13. The connecting elements can hold the edge of each disc in several points as shown in FIG. 11. On the other hand, while in FIG. 11 the connecting elements hold the inner edges of the discs, they can also hold the outer edge of each disc as shown in FIG. 12. In this case they also connect the outer edges of the discs to the inner surface of the container. Upon nesting or engaging of the connecting elements with the discs held in them with one another, a packet of the discs is assembled. The packet is then inserted in the inner chamber of the container and held there. The connecting elements serve not only for connecting the discs with one another, but also for arranging them at a certain distance from one another, thus performing both the connecting functions and the spacing functions. As can be shown from FIG. 14, the connecting elements can have an L-shaped main portion.

While the invention has been illustrated and described as embodied in a specific device for growing cells, it is not intended to be limited to the details shown, since various modifications and structural changes are possible without departing in any way from the spirit of the present invention.

The foregoing will so fully reveal the gist of the present invention that other can readily adapt it for various applications without omitting features that, from the standpoint of prior art, fairly constitute essential characteristics of the generic or specific aspects of this invention.

What is claimed as new and desired to be protected by Letters Patent is set forth in particular in the appended claims.

I claim:

1. A device for growing cells, comprising a container having a longitudinal axis and forming an inner chamber;

a plurality of discs for supporting cells, said discs being located in said inner chamber of said container substantially coaxially with the latter and being spaced from one another in an axial direction, each of said discs being provided with corrugations sufficient to entrain a growth medium with cells during rotation of said discs around said axis while allowing the growth medium with the cells to move radially inwardly over said discs; and means for connecting said discs with one another.

2. A device for growing cells as defined in claim 1, wherein said discs are located axially close together so that projections of said corrugations of one of said discs are inserted into grooves of said corrugations of a neighboring one of said discs, and thereby a serpentine path for flowing of the growth medium between said corrugations of neighboring ones of said discs is formed.

3. A device for growing cells as defined in claim 1, wherein said connecting means includes a shaft, each of said discs having a central opening so that said discs can be arranged on said shaft by passing said shaft through said central openings of said discs.

4. A device for growing cells as defined in claim 3, wherein said shaft has a peripheral projection extending in an axial direction while each of said discs has a peripheral groove communicating with each of said central openings so that said peripheral projection of said shaft engages in said grooves of said discs.

5. A device for growing cells as defined in claim 3, further comprising means for spacing said discs from one another, said spacing means comprising a plurality of spacers arranged between said discs.

6. A device for growing cells as defined in claim 5, wherein each of said spacers has a central hole so that said shaft can pass through said central holes of said spacers, said shaft has a peripheral projection extending substantially in an axial direction, and each of said spacers also has a groove communicating with said central holes and formed so that said peripheral projection of said shaft can engage in said grooves of said spacers.

7. A device for growing cells as defined in claim 1, wherein each of said discs has a disc-shaped portion and a hub portion, said hub portions of said discs being nestable in one another so as to form said connecting means.

8. A device for growing cells as defined in claim 1, wherein said connecting means include a plurality of connectors each connected with a respective one of said discs and connectable with one another.

9. A device for growing cells as defined in claim 8, wherein said connectors are formed so that they not only connect said discs with one another but also hold said discs at a distance from one another so as to form spacers.

10. A device for growing cells as defined in claim 8, wherein each of said discs has an outer edge which faces toward said container and an inner edge which defines an inner hole, said connectors of said connecting means being connected with each of said discs at one of said edges.

11. A device for growing cells as defined in claim 10, wherein said connectors of said connecting means are connected with said inner edges of said discs.

12. A device for growing cells as defined in claim 10, wherein said connectors are connected with said outer edges of said discs and also with an inner wall of said container so as to connect said outer edges of said discs with said container.

* * * * *